United States Patent [19]
Silverman et al.

[11] Patent Number: 5,906,983
[45] Date of Patent: May 25, 1999

[54] HIGH FRUCTOSE CONTAINING INSECTICIDE COMPOSITIONS AND METHODS OF USING THE SAME

[75] Inventors: Jules Silverman, Walnut Creek, Calif.; Donald N. Bieman, Cayey, Puerto Rico

[73] Assignee: The Clorox Company, Oakland, Calif.

[21] Appl. No.: 08/915,110

[22] Filed: Aug. 20, 1997

[51] Int. Cl.$^6$ .......................... A01N 25/00; A01N 43/56; A01N 57/00
[52] U.S. Cl. .............................. 514/89; 424/84; 514/406; 514/407
[58] Field of Search ............................ 514/89, 406, 407; 424/84

[56] References Cited

U.S. PATENT DOCUMENTS

| | | | |
|---|---|---|---|
| Re. 30,740 | 9/1981 | Frensch et al. | 424/276 |
| 3,630,446 | 12/1971 | Roth et al. | 424/219 |
| 3,636,207 | 1/1972 | Bouvet et al. | 424/219 |
| 3,937,826 | 2/1976 | Harris | 424/17 |
| 3,952,102 | 4/1976 | Albrecht et al. | 424/276 |
| 3,961,040 | 6/1976 | Rabussier et al. | 424/78 |
| 3,996,375 | 12/1976 | Frensch et al. | 424/276 |
| 4,278,014 | 7/1981 | Knieps | 100/26 |
| 4,320,130 | 3/1982 | Balsley et al. | 424/251 |
| 4,349,981 | 9/1982 | Sherman | 43/131 |
| 4,353,907 | 10/1982 | Lovell | 424/251 |
| 4,368,591 | 1/1983 | Barke et al. | 47/57.6 |
| 4,510,133 | 4/1985 | Evans | 514/30 |
| 4,560,677 | 12/1985 | Dybas | 514/30 |
| 4,626,528 | 12/1986 | McHenry | 514/119 |
| 4,657,912 | 4/1987 | Suzuki et al. | 514/275 |
| 4,681,900 | 7/1987 | Iwasaki | 514/567 |
| 4,696,822 | 9/1987 | Matsumura et al. | 424/490 |
| 4,721,706 | 1/1988 | Bessler et al. | 514/78 |
| 4,750,934 | 6/1988 | Metzner et al. | 106/18 |
| 4,796,381 | 1/1989 | Kauth et al. | 43/124 |
| 4,834,977 | 5/1989 | Kohama et al. | 424/405 |
| 4,874,611 | 10/1989 | Wilson et al. | 424/410 |
| 4,889,710 | 12/1989 | Hagarty | 424/45 |
| 4,902,510 | 2/1990 | Garden | 424/405 |
| 4,929,608 | 5/1990 | Mahmood | 514/122 |
| 4,950,682 | 8/1990 | Pap et al. | 514/417 |
| 4,985,413 | 1/1991 | Kohama et al. | 424/84 |
| 4,996,053 | 2/1991 | Hatcher | 424/410 |
| 5,023,183 | 6/1991 | Friedman et al. | 435/240.3 |
| 5,026,734 | 6/1991 | Browning | 514/723 |
| 5,063,084 | 11/1991 | Nelson | 427/154 |
| 5,120,540 | 6/1992 | Doane et al. | 424/195.1 |
| 5,130,135 | 7/1992 | Van Tonder | 424/405 |
| 5,196,407 | 3/1993 | Goletz et al. | 514/63 |
| 5,198,467 | 3/1993 | Milks | 514/553 |
| 5,221,535 | 6/1993 | Domb | 424/450 |
| 5,223,270 | 6/1993 | Jones | 424/659 |
| 5,248,086 | 9/1993 | Waldrum et al. | 239/10 |
| 5,248,450 | 9/1993 | Metzner et al. | 252/300 |
| 5,271,179 | 12/1993 | Cohen | 43/131 |
| 5,401,506 | 3/1995 | Chang et al. | 424/408 |
| 5,417,973 | 5/1995 | King | 424/195.1 |
| 5,435,992 | 7/1995 | Audegond et al. | 514/419 |
| 5,439,683 | 8/1995 | Hodakowski | 424/408 |
| 5,464,613 | 11/1995 | Barcay et al. | 424/84 |
| 5,464,618 | 11/1995 | Doane et al. | 424/195.1 |
| 5,554,576 | 9/1996 | Mookerjee et al. | 504/116 |
| 5,580,567 | 12/1996 | Roberts | 424/405 |

OTHER PUBLICATIONS

Abstract of EP 311 180 (Apr. 12, 1989).
Abstract of GB 2,113,092 (Aug. 3, 1983).
Abstract of GB 2,058,569 (Apr. 15, 1981).
Abstract of JP 61–254507 (Nov. 12, 1986).
Abstract of JP 61–22003 (Jan. 30, 1986).
Abstract of JP 60–255701 (Dec. 17, 1985).
Abstract of JP 57–171906 (Oct. 22, 1982).
Abstract of JP 57–154113 (Sep. 22, 1982).
Abstract of JP 56–169601 (Dec. 26, 1981).
Abstract of JP 56–138105 (Oct. 28, 1981).
Abstract of JP 56–65808 (Jun. 3, 1981).
Abstract of JP 56–8308 (Jan. 28, 1981).
Abstract of JP 55–31053 (Mar. 5, 1980).
Abstract of JP 07–304603 (Nov. 21, 1995).
Abstract of JP 02–307912 (Dec. 21, 1990).
Abstract of JP 02–207009 (Aug. 16, 1990).
Abstract of JP 02–67204 (Mar. 7, 1990).
Abstract of JP 02–67203 (Mar. 7, 1990).
Abstract of JP 01–301605 (Dec. 5, 1989).
Abstract of JP 01–151501 (Jun. 14, 1989).
Abstract of JP 01–38004 (Feb. 8, 1989).
Abstract of JP 63–218604 (Sep. 12, 1988).
Abstract of JP 62–198602 (Sep. 2, 1987).
Abstract of Jp 62–195301 (Aug. 28, 1987).
Abstract of WO 92/19429 (Nov. 12, 1992).
Abstract of WO 92/10170 (Jun. 25, 1992).
Abstract of WO 96/31123 (Oct. 10, 1996).
Philip G. Koehler et al., "Control of German Cockroach (Dictyoptera: Blattellidae) with Residual Toxicants in Bait Trays", *Journal of Economic Entomology*, vol. 89, No. 6, pp. 1491–1496 (1996).

*Primary Examiner*—Allen J. Robinson
*Attorney, Agent, or Firm*—Harry A. Pacini; Mark Sweet

[57] ABSTRACT

A composition effective for the control of insects is disclosed, wherein the composition contains a phenyl pyrazole compound or a halopyridyl compound, and a food attractant containing at least one saccharide where the composition is free or substantially free of glucose. Also disclosed is a method of applying the composition to an area where the insects are to be controlled.

29 Claims, No Drawings

HIGH FRUCTOSE CONTAINING INSECTICIDE COMPOSITIONS AND METHODS OF USING THE SAME

FIELD OF THE INVENTION

Our discovery relates to compositions effective for controlling insects, and more particularly, compositions containing a phenyl pyrazole compound or a halopyridyl compound, and a food attractant containing high levels of fructose and low levels of glucose for the control of the cockroaches.

BACKGROUND OF INVENTION

Compositions for controlling insects such as cockroaches are known in the art. Generally, the compositions contain at least one substance toxic to the insects, and additionally some type of food attractant. Most toxic substances, also known as toxicants, are based on chemicals which are either capable of instant and/or delayed killing action. The food attractants used include various sweetening agents, together with the toxicant. The prior art describes insecticide bait compositions containing a very general array of sugars and sweeteners as food attractants for cockroach control, without regard to diversity of feeding preferences by field cockroach strains.

For example, U.S. Pat. No. 4,386,071 relates to an insecticide natural bait composition which includes, in a broad sense, sugar or sugar substitute. Similarly, U.S. Pat. No. 4,845,103 relates to an insecticide bait composition for the control of cockroaches in which the food attractant system comprises various ingredients, including a mixture of liquid food, for example, molasses, corn syrup, maple syrup, or honey.

U.S. Pat. No. 4,889,710 relates to a stable aerosol foam insecticide bait composition which includes a food attractant to facilitate consumption by the crawling insects, sugars or a sugar composition.

U.S. Pat. No. 4,985,413 relates to poison bait for control of insects, particularly cockroaches, wherein the bait contains a saccharide as a component in an amount of 10–40% by weight based on the total weight of the composition. Examples of saccharide in the '413 patent are sucrose, glucose, d-fructose, lactose, black sugar, brown sugar, and soft brown sugar. Among the preferred sugars mentioned in the '413 patent are black sugar, brown sugar and soft brown sugar. The content of the saccharide is normally preferred between 10–40% by weight.

In U.S. Pat. No. 5,547,955, we previously detailed the unexpected superior results of insecticidal bait compositions having a high ratio of fructose to glucose, without regard to the toxic substance within the compositions. Despite the fact that glucose is considered the universal metabolic fuel and one of the most common substances used to attract insects to toxicants, we found that glucose actually repels certain strains of cockroaches.

OBJECTS OF THE INVENTION

An object of the invention is to provide a composition suitable for use in controlling insects, particularly cockroaches.

Another object of the invention is to provide a composition having superior efficacy for controlling insects, particularly cockroaches.

Another object of the invention is to provide a method of controlling insects having superior efficacy, particularly for controlling cockroaches.

SUMMARY OF THE INVENTION

To achieve these and other objectives, and in accordance with the purpose of our invention as embodied and broadly described herein, in one aspect we describe a composition containing an effective amount of a phenyl pyrazole compound or a halopyridyl compound, and a food attractant containing at least one saccharide wherein the composition is free or substantially free of glucose.

In another aspect we describe a method of controlling insects, where the method includes the application of an effective amount of a phenyl pyrazole compound or a halopyridyl compound, and a food attractant containing at least one saccharide and is free or substantially free of glucose.

DETAILED DESCRIPTION OF THE INVENTION

We have now found that particular compositions containing at least one saccharide as a food attractant, where the compositions are free or substantially free of glucose, unexpectedly have superior efficacy. By "free or substantially free," as used herein, we mean that the food attractant has a ratio of fructose to glucose in excess of about 9:1. Specifically, our compositions having this unexpectedly superior efficacy also contain a phenyl pyrazole compound or a halopyridyl compound as the toxicant.

As used herein, "a phenyl pyrazole compound" refers to the compounds referred to as N-phenylpyrazole derivatives in U.S. Pat. No. 5,232,940. The entire contents of the '940 patent are incorporated herein by reference.

More specifically, the phenyl pyrazole compound used in our composition will have the following chemical structure,

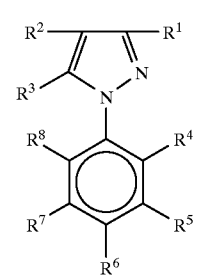

(I)

wherein $R^1$ represents a cyano or nitro group, a halogen, i.e. fluorine, chlorine, bromine or iodine atom, an acetyl or formyl group, a straight- or branched-chain alkyl group containing from 1 to 4 carbon atoms which may be unsubstituted or substituted by one or more halogen atoms or a cycloalkyl group containing from 3 to 6 carbon atoms; $R^2$ represents a group R'SO$_2$, R'SO, or R'S in which R' represents a straight- or branched-chain alkyl, alkenyl or alkynyl (preferably 1-(alkynyl)alkyl and more preferably alk-2-ynyl) group containing up to 6 carbon atoms which may be unsubstituted or substituted by one or more halogen atoms which may be the same or different; or $R^2$ is a halogen, i.e., fluorine, chlorine, bromine or iodine atom, a cyano or nitro group, a cycloalkyl group containing from 3 to 5 carbon atoms, a straight- or branched-chain alkenyl group containing from 2 to 6 carbon atoms, a thiocyanato group, a sulphamoyl group which may be unsubstituted or substituted by one or two straight- or branched-chain alkyl groups which may be the same or different and contain from 1 to 6 carbon atoms, a carbamoyl group which may be unsubstituted or substituted by one or two straight- or branched-chain alkyl groups which may be the same or different and contain from 1 to 6 carbon atoms, a straight- or branched-chain alkoxycarbonyl containing from 2 to 7 carbon atoms, a straight- or branched-chain alkanoyl group containing from 2 to 7 carbon atoms, or a straight- or branched-chain alkyl group containing from 1 to 6 carbon atoms which may be unsubstituted or substituted by one or more halogen atoms; $R^3$ represents a hydrogen atom, or an amino group —NR"R'" wherein R" and R'", which may be the same or different, each represent a hydrogen atom or a straight- or branched-chain alkenylalkyl or alkynylalkyl group containing up to 5 carbon atoms, a straight- or branched-chain alkyl group (containing from 1 to 6 carbon atoms, and which may be unsubstituted or substituted by straight- or branched-chain alkoxycarbonyl of 2 to 5 carbon atoms), a formyl group, a straight- or branched-chain alkanoyl group (which contains from 2 to 7 carbon atoms and which may be optionally substituted with one or more halogen atoms) or R" and R'", together with the nitrogen atom to which they are attached, form a 5 to 6 membered cyclic imide and is unsubstituted or substituted with one or more halogen atoms, or $R^3$ represents a straight- or branched-chain alkoxycarbonyl group (which contains from 2 to 7 carbon atoms and is unsubstituted or substituted by one or more halogen atoms), or $R^3$ represents a straight- or branched-chain alkoxymethyleneamino group containing from 2 to 5 carbon atoms which may be unsubstituted or substituted on methylene by a straight- or branched-chain alkyl group containing from 1 to 4 carbon atoms, or $R^3$ represents a halogen, i.e., fluorine, chlorine, bromine or iodine, a cycloalkyl group containing from 3 to 6 carbon atoms, or cycloakylcarbonyl group (which contains from 4 to 7 carbon atoms) or straight- or branched-chain alkoxy carbonyl group (which contains from 2 to 7 carbon atoms which are unsubstituted or substituted by one or more halogen atoms), or $R^3$ represents a straight- or branched-chain alkylsulphenylamino group containing from 1 to 4 carbon atoms, or $R^3$ represents a straight- or branched-chain alkyl group containing from 1 to 4 carbon atoms, the carboxy group or a straight-branched chain alkylthio, alkylsulphinyl or alkysulphonyl group containing from 1 to 6 carbon atoms which may be unsubstituted or substituted by one or more halogen atoms, or $R^3$ represents a straight- or branched-chained trialkylsilylm-ethyl group containing from 1 to 6 carbon atoms in each alkyl group which may be the same or different, a trialkyl-silyl group containing from 1 to 6 carbon atoms in each alkyl group which may be the same or different, or the cyano or nitro group; $R^4$, $R^5$, $R^6$, $R^7$ and $R^8$ may be the same or different and represent a halogen, i.e., fluorine, chlorine, bromine or iodine, a straight- or branched-chain alkyl or alkoxy group containing from 1 to 4 carbon atoms which may be unsubstituted or substituted by one or more halogen atoms (e.g. a trifluoromethyl or trifluoromethoxy group), a straight- or branched-chain alkylthio or alkylsulphinyl group containing from 1 to 4 carbon atoms which is substituted by one or more halogen atoms (e.g. a trifluoromethylthio or trifluoromethylsulphinyl group), the nitro or cyano group or a straight- or branched-chain alkylsulphonyl group containing from 1 to 4 carbon atoms which may be unsubstituted or substituted by one or more halogen atoms (e.g. the trifluoromethylsulphonyl group).

Preferably, phenyl pyrazole compounds of the above formula are used wherein $R^1$ represents a cyano or nitro group, a halogen, i.e., fluorine, chlorine, bromine, or iodine, atom, or an acetyl or formyl group; $R^2$ represents group R'SO$_2$, R'SO, or R'S in which R' represents a straight or branched chain alkyl, alkenyl or alkynyl (preferably 1-(alkynyl) alkyl and more preferably alk-2-ynyl) group containing up to 4 carbon atoms which may be unsubstituted or substituted by one or more halogen atoms which may be the same of different; $R^3$ represents a hydrogen atom, or an amino group —NR'R'" wherein R" and R'", which may be the same or different, each represent a hydrogen atom or a straight or branched chain alkyl, alkenyl or alkynylalkyl group containing up to 5 carbon atoms, a formyl group, a straight or branched chain alkanoyl group (which contains from 2 to 5 carbon atoms and which may be optionally substituted by one or more halogens atoms) or R" and R'" together with the nitrogen atom to which they are attached form a 5 or 6 membered cyclic imide, or represents a straight or branched-chain alkoxycarbonyl group (which contains 2 to 5 carbon atoms and is unsubstituted or substituted by one or more halogen atoms), or $R^3$ represents a straight or branched-chain alkoxymethyleneamino group containing from 2 to 5 carbon atoms which may be unsubstituted or substituted on methylene by a straight or branched-chain alkyl group containing from 1 to 4 carbon atoms, or represent a halogen, i.e., fluorine, chlorine, bromine or iodine; and $R^4$ is a fluorine, chlorine, bromine or iodine; $R^6$ is a straight or branched chain alkyl or alkoxy group containing from 1 to 4 carbon atoms which may be unsubstituted or substituted by one or more halogen atoms which may be the same or different (the trifluoromethyl and trifluoromethoxy groups are preferred), or a chlorine or bromine atom; and $R^8$ is hydrogen or a fluorine, chlorine, bromine or iodine atom, with the exclusion of the compound wherein $R^1$ represents cyano, $R^2$ represents methanesulphonyl, $R^3$ represents amino, $R^4$ and $R^8$ are chloro and $R^6$ is trifluoromethyl (i.e., the phenyl ring is 2,6-dichloro-4-tri-fluoromethylphenyl), which have valuable activity against arthropod, plant nematode, helminth and protozoan pests, more particularly by ingestion of above preferred compound(s) by the arthropods.

Preferred compounds of the first embodiment of general formula I also include those wherein $R^2$ represents an alkylsuphonyl/sulphinyl/thio group which is optionally halogen substituted containing from 1 to 4 carbon atoms, or an alkenyl- or alkynyl-sulphonyl/sulphinyl/thio group which is optionally halogen substituted and contains up to 4 carbon atoms, preferably a trifluoromethylthio or trifluoro methyl-sulphinyl group, $R^3$ represents the hydrogen atom, an amino or methylamino group and $R^1$ represents a halogen atom or preferably the cyano or nitro group.

Compounds of general formula I wherein the phenyl group contains the trifluoromethyl or trifluoromethoxy group, and $R^2$ represents an optionally halogenated alkylsulphonyl/sulphinyl/thio group containing from 1 to 4 carbon atoms are also preferred. Trifluoromethylthio, trifluoromethylsulphinyl, and trifluoromethanesulphonyl are especially preferred for $R^2$.

Preferred compounds of the first embodiment of general formula I also include those with phenyl substitution which is 2,4,6-trichloro, 2,6-dichloro-4-difluoromethoxy, 2-chloro-4-trifluoromethyl, 2-bromo-6-chloro-4-trifluoromethyl, 2,6-dibromo-4-trifluoromethyl or 2-bromo-4-trifluoromethyl.

In a most preferred embodiment, the composition comprises the phenyl pyrazole compound known as fipronil, which has the following chemical structure:

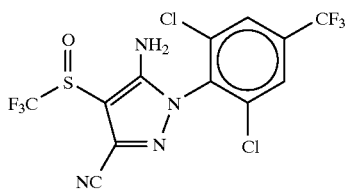

A preferred embodiment of the invention includes compositions having about 0.001 percent by weight to about 1.0 percent by weight of the phenyl pyrazole compound, and about 10 percent by weight to about 90 percent by weight of the saccharide composition. A more preferred embodiment includes compositions having about 0.01 percent by weight to about 0.1 percent by weight of the phenyl pyrazole compound, and about 20 percent by weight to about 60 percent by weight of the food attractant.

A "halopyridyl compound," as used herein, refers to the compounds described as halopyridyl compounds in U.S. Pat. No. 3,244,586, the entire contents of which are incorporated herein by reference.

More specifically, the halopyridyl compound used in our composition will have the following chemical structure:

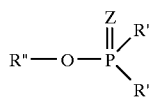

wherein R" represents halopyridyl, Z is selected from the group consisting of oxygen and sulfur, and each R' is individually selected from the group consisting of lower alkoxy, amino, and lower alkylamino.

Preferably, the halopyridyl compound is chlorpyrifos, which has the following chemical structure:

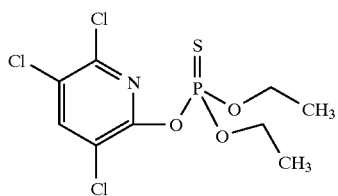

The halopyridyl compound may be present in our composition in an amount ranging from about 0.01 percent by weight to about 5.0 percent by weight. Preferably, the halopyridyl is present at about 0.1 percent by weight to about 1.0 percent by weight.

The composition may additionally contain a binder. The binder may be, for example, oatmeal, Elmer's glue, polyvinyl acetate emulsion-based glues, acetate emulsion glues, polyvinyl acetate emulsions, natural glues such as beef collagen, Carragennan, and water-absorbing polymers, waxes such as paraffin, ceresin wax, candilla wax, POLAWAX, beeswax, carnauba wax, microcrystalline waxes, and polyethylene waxes, glyceryl monostearate, polyethylene glycols, such as PEG™ 8000, and combinations thereof. Typically, the binder is present in the composition from about 5.0 to about 20 percent by weight, preferably about 8.0 to about 15 percent by weight. Preferably, the binder chosen is not a repellant to the target insect.

Antimicrobial agents also may be included in the composition. Optionally, from about 0.1 percent by weight to about 2.0 percent by weight of an antimicrobial agent. Preferably, the composition contains about 0.2 to about 1.0 percent by weight of an antimicrobial agent such as sorbic acid/potassium sorbate, potassium sulfate, Dowcil™ 200 (cis isomer of 2-(3-chloroallyl) 3,5,7-triaza-1-azonia-1-adamantane chloride), sodium salicylate, esters of p-hydroxybenzoic acid such as propyl paraben/methyl paraben (propyl P-hydroxy benzoate/methyl p-hydroxybenzoate), Captan™ (N-(trichloromethylthio)-4-cyclohexane-1,3-di-carboximide), sodium silicate, sodium dehydroaceate and sodium benzoate, bromo-nitro propane diols such as 2-bromopropane 1,3-diol, 3-iodo-2-propylbutyl carbamate; benzo-thiazolin-2-one, or combinations thereof. These may be added as preservatives to inhibit microorganism growth and may be incorporated during formation of the composition of this invention.

Our composition may additionally contain food attractants other than the saccharide composition described herein. For example, proteins, carbohydrates, and lipids may be included in the composition. Preferably, the composition contains edible oils such as soybean oils, spray dried poultry liver, oatmeal, molasses, rice bran oil, fishmeal, silkworm pupae, or combinations thereof. The amount of food attractants other than saccharides may range from about 50 to 80 percent by weight, preferably 60–75 percent by weight of the composition.

The composition may also contain anti-oxidants that are well known in the art. An example of such an anti-oxidant is sold under the brandname T-BHQ™. The anti-oxidant may be present in an amount ranging from about 0.05 to about 0.5 percent by weight, preferably about 0.1 to about 0.3 percent by weight.

Our composition may additionally contain solvents effective to dissolve the active ingredient. Such solvents include, for example, acetone, dichloromethane, ethyl acetate, oleic acid, methanol, 1-octanol, 2-propanol, N-methyl pyrrolidone, propylene glycol, and ethanol or combinations thereof. About 1.0 to about 10 percent by weight of the solvent may be present in the composition, preferably about 2.0 to about 6.0 percent by weight.

Added water may also be present in the composition, in an amount ranging from about 0.1 to about 5.0 percent by weight, preferably 0.2 to about 2.0 percent by weight.

The composition may be applied in any manner to the area where insects, particularly crawling insects such as cockroaches, are to be controlled. Such applications broadly include direct application to surfaces within the area with a syringe or similar device. Additionally, our composition may be applied to a substrate which is then placed within the area to be treated.

The composition may also be applied to the area in combination with a "bait station." These bait stations, typically made of plastic, are well known in the art.

EXAMPLE 1

Insecticide/corn syrup compositions shown in Table 1 were tested for efficacy. The "fructose" corn syrup tested contained about 95 to about 100 percent by weight fructose, and is sold as the brandname Krystar™. The "fructose/glucose" corn syrup contained 55 percent by weight fructose, 42 percent by weight glucose, and 3 percent by weight higher saccharides, and is sold under th brandname CornSweet55™.

The testing arena was two 18"×12"×8" plastic containers attached end-to-end via a ¾" diameter×2" long Tygon tube. A cardboard harborage was placed in one container with 30 German cockroaches (T-164 strain). The test bait was placed in the opposite arena. Free access was provided through the Tygon tube. Water and food was placed in both containers. Three replicates per treatment were performed. Dead cockroaches were counted, recorded and removed at each of 4 time points. Results:

TABLE 1

| | | Cumulative % Mortality At Day | | | | |
|---|---|---|---|---|---|---|
| Insecticide | Corn Syrup | 1 | 2 | 3 | 4 | 5 |
| Fipronil | Fructose | 41 | 62 | 69 | 87 | 92 |
| Fipronil | Fructose/glucose | 9 | 33 | 42 | 64 | 66 |
| Chlorpyrifos | Fructose | 11 | 23 | 28 | 43 | 47 |
| Chlorpyrifos | Fructose/glucose | 0 | 0 | 1 | 1 | 1 |

The best performance was provided by fipronil mixed with high fructose corn syrup. This composition resulted in an unexpectedly higher mortality rate as compared to the chlorpyrifos/fructose composition and the fipronil/fructose/glucose composition.

It will be apparent to those skilled in the art that various modifications and variations can be made in the composition and method disclosed above without departing from the spirit of our discovery. Thus, it is intended that our description covers the modifications and variations of this invention provided that they come within the scope of the appended claims and their equivalents.

We claim:

1. A composition comprising about 0.001 percent by weight to about 1.0 percent by weight of a phenyl pyrazole compound or about 0.01 percent by weight to about 5.0 percent by weight of a halopyridyl compound, and a food attractant which comprises at least one saccharides, wherein the food attractant has a ratio of fructose to glucose in excess of about 9:1.

2. The composition of claim 1, wherein the composition contains a phenyl pyrazole compound having the following structure:

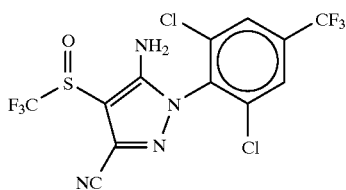

3. The composition of claim 1, wherein the composition contains a halopyridyl compound having the following structure:

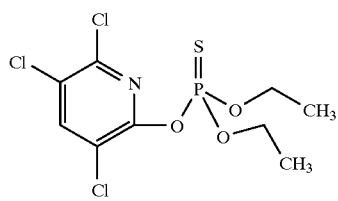

4. The composition of claim 1, wherein the saccharide is free of glucose.

5. The composition of claim 1 wherein the saccharide comprises fructose, sucrose, maltose, or combinations thereof.

6. The composition of claim 1, wherein the composition is a cockroach bait composition and is free or substantially free of repellency characteristics.

7. The composition of claim 1, wherein the saccharide composition is present in an amount of about 10 percent by weight to about 90 percent by weight.

8. The composition of claim 1, further comprising a binder, an antimicrobial agent, an additional food attractant, a solvent, and an antioxidant.

9. The composition of claim 1, wherein the composition is located on a substrate.

10. The composition of claim 9, wherein the substrate is a non-absorbent material.

11. The composition of claim 9, wherein the substrate is cardboard or plastic.

12. The composition of claim 1, wherein the phenyl pyrazole compound is present in an amount of about 0.01 percent by weight to about 0.1 percent by weight.

13. The composition of claim 1, wherein the halopyridyl compound is present in an amount of about 0.1 percent by weight to about 1.0 percent by weight.

14. A method of controlling insects comprising applying an effective amount of the composition as claimed in claim 1 to an area where the insects are to be controlled.

15. The method of claim 1, wherein the composition contains a phenyl pyrazole compound having the following structure:

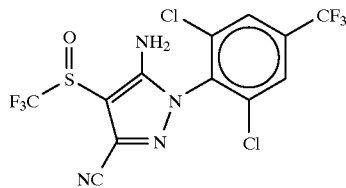

16. The method of claim 14, wherein the composition contains a halopyridyl compound having the following structure:

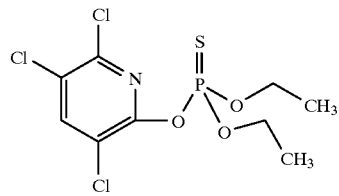

17. The method of claim 14, wherein the saccharide is free of glucose.

18. The method of claim 14, wherein the saccharide comprises fructose, sucrose, maltose, or combinations thereof.

19. The method of claim 14, wherein the composition is applied to at least one surface within the area.

20. The method of claim 14, wherein the composition is first applied to a substrate, and then the substrate is placed within the area.

21. The method of claim 20, wherein the substrate is a non-absorbent material.

22. The method of claim 20, wherein the substrate is cardboard or plastic.

23. The method of claim 14, wherein the composition is directly applied to at least one surface within the area.

24. The mehtod of claim 14, wherein the saccharide composition is present in an amount of about 10 percent by weight to about 90 percent by weight.

25. The method of claim 14, wherein the insects are cockroaches.

26. The method of claim 25, wherein the cockroaches are *Blattella germanica.*

27. The method of claim 25, wherein the cockroaches are the T-164 strain.

28. The method of claim 14, wherein the phenyl pyrazole compound is present in an amount of about 0.01 percent by weight to about 0.1 percent by weight.

29. The method of claim 14, wherein the halopyridyl compound is present in an amount of about 0.1 percent by weight to about 10 percent by weight.

* * * * *